ns011335458B2

United States Patent
Stohlein et al.

(10) Patent No.: US 11,335,458 B2
(45) Date of Patent: May 17, 2022

(54) DEVICE FOR TRANSMITTING OPERATING AND MACHINE DATA OF A MEDICAL APPARATUS, MEDICAL APPARATUS, AND METHOD FOR TRANSMITTING OPERATING AND MACHINE DATA OF A MEDICAL APPARATUS

(71) Applicant: FRESENIUS MEDICAL CARE DEUTSCHLAND GMBH, Bad Homburg (DE)

(72) Inventors: Dieter Stohlein, Kohlitzheim/Herlheim (DE); Jurgen Schuller, Bad Konigshofen (DE); Achim Eberlein, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 253 days.

(21) Appl. No.: 16/473,629

(22) PCT Filed: Dec. 29, 2017

(86) PCT No.: PCT/EP2017/084790
§ 371 (c)(1),
(2) Date: Jun. 26, 2019

(87) PCT Pub. No.: WO2018/122364
PCT Pub. Date: Jul. 5, 2018

(65) Prior Publication Data
US 2019/0341144 A1 Nov. 7, 2019

(30) Foreign Application Priority Data
Dec. 30, 2016 (DE) ...................... 10 2016 125 951.9

(51) Int. Cl.
*G16H 40/40* (2018.01)
*G16H 20/17* (2018.01)
*A61M 1/14* (2006.01)

(52) U.S. Cl.
CPC ............... *G16H 40/40* (2018.01); *A61M 1/14* (2013.01); *G16H 20/17* (2018.01)

(58) Field of Classification Search
CPC .................................................... G16H 40/40
See application file for complete search history.

(56) References Cited

U.S. PATENT DOCUMENTS 8,217,781 B2 7/2012 Ebrom et al.
10,173,008 B2 * 1/2019 Simpson ................ G16H 20/10
(Continued)

FOREIGN PATENT DOCUMENTS

EP 0597817 A2 5/1994
GB 2225459 A 5/1990
(Continued)

OTHER PUBLICATIONS

Examination Report issued in corresponding German Patent Application No. 10 2016 125 951.9 dated Jun. 20, 2017 (4 pages).
(Continued)

*Primary Examiner* — Robert A Sorey
*Assistant Examiner* — Kristine K Rapillo
(74) *Attorney, Agent, or Firm* — Kilyk & Bowersox, P.L.L.C.

(57) ABSTRACT

The invention relates to an apparatus (100) for transmitting operating and machine data of a medical device (500), preferably a dialysis device, to an evaluation device (60), wherein the apparatus (100) comprises a data input (12) for receiving operating and machine data of the medical device (500), a programmable storage unit (20) which is configured to store at least a portion of the operating and machine data (Continued)

that is received, a voltage input (11) which is configured to supply the apparatus (100) with an operating voltage provided by the medical device (500), and a transmission unit (30) which is configured to transmit the stored operating and machine data to the evaluation device (60).

15 Claims, 5 Drawing Sheets

(56) References Cited

U.S. PATENT DOCUMENTS

| | | | |
|---|---|---|---|
| 10,569,007 B2* | 2/2020 | Hobro | A61M 1/14 |
| 2008/0287121 A1 | 11/2008 | Ebrom et al. | |
| 2009/0069642 A1 | 3/2009 | Gao et al. | |
| 2009/0100132 A1* | 4/2009 | Ebrom | G04R 20/26 |
| | | | 709/203 |
| 2010/0168653 A1 | 7/2010 | Levin | |
| 2011/0185035 A1 | 7/2011 | Van | |
| 2013/0283196 A1* | 10/2013 | Farnan | G06F 3/04847 |
| | | | 715/771 |
| 2015/0365507 A1 | 12/2015 | Vasapollo | |

FOREIGN PATENT DOCUMENTS

| | | |
|---|---|---|
| GB | 2329983 A | 4/1999 |
| WO | 9610233 A1 | 4/1996 |

OTHER PUBLICATIONS

Nguyen et al., "Cloud-based Secure Logger For Medical Devices," Proceedings of the 2016 IEEE First Conference on Connected Health: Applications, Systems and Engineering Technologies, DOI 10.1109/CHASE.2016.48, 2016, pp. 89-94.

Wikipedia, Dongle, Artikel zum Begriff "Dongle," vom Oct. 3, 2016 [recherchiert am Feb. 13, 2017], 5 pages.

International Search Report and Written Opinion issued in corresponding International Patent Application No. PCT/EP2017/084790 (with English translation of International Search Report) dated Apr. 10, 2018 (13 pages).

International Preliminary Report on Patentability issued in corresponding International Patent Application No. PCT/EP2017/084790 dated Jul. 11, 2019 (6 pages).

* cited by examiner

DEVICE FOR TRANSMITTING OPERATING AND MACHINE DATA OF A MEDICAL APPARATUS, MEDICAL APPARATUS, AND METHOD FOR TRANSMITTING OPERATING AND MACHINE DATA OF A MEDICAL APPARATUS

This application is a National Stage Application of PCT/EP2017/084790, filed Dec. 29, 2017, which claims priority to German Patent Application No. 10 2016 125 951.9, filed Dec. 30, 2016.

TECHNICAL FIELD

The present invention relates to an apparatus for transmitting operating and machine data of a medical device to an evaluation device, a medical device, and a method for transmitting operating and machine data of a medical device to an evaluation device. The medical device is preferably a device for extracorporeal blood treatment, for example a dialysis device for performing hemodialysis, hemofiltration, hemodiafiltration and/or another dialysis treatment. The medical device can also be a peritoneal dialysis device, an acute dialysis device, a liver assist therapy device or an apheresis device.

A medical device can generate operating and machine data during its operation, for example when a dialysis treatment is carried out, but also in other operating states of the medical device. The operating and machine data can be used, for example, to identify wear in components of the medical device, and/or impaired functionality of components. The support of a service technician may then be necessary in order to determine and rectify the cause. In some cases, the operating and machine data that is generated may not be sufficient to enable a service technician onsite to determine and rectify the cause, in which case the support of the manufacturer of the medical device, or the manufacturer's development department, is desirable. For this purpose it is helpful to record or log the operating and machine data of the medical device, preferably selectively. To view and analyze the operating and machine data, the manufacturer, and in particular its development department, can use for example a software tool which offers special means of visualization in order to facilitate the identification of causes using other analytical means.

TECHNICAL BACKGROUND

Previously, the recording of operating and machine data that is to be viewed and analyzed has been carried out using, for example, a portable or laptop computer which is connected with the medical device. It is, however, not always possible or desirable for safety reasons to connect a computer with the medical device during treatment operations, in particular during a medical dialysis treatment. Furthermore, the portable computer requires an energy supply unit that is specially approved for medical applications. As a result, it may for example not be possible to record operating and machine data that is captured during operation.

Patent specification U.S. Pat. No. 8,217,781 B2 describes a method of facilitating the servicing of a domestic appliance. The application document US 2011/185035 A1 describes a causal analysis device for medical equipment. The application documents GB 2 329 983 A, GB 2 225 459 A, EP 0 597 817 A2 and WO 96/10233 A1 describe data loggers and/or detachable data loggers.

DESCRIPTION OF THE INVENTION

For rapid and simplified determination and rectification of causes, it is desirable to record operating and machine data also during the operation of the medical device.

The term "operation of the medical device" is to be understood here and hereinafter as treatment of a patient. Operation is in particular to be differentiated from, for example, maintenance, during which no patient is treated and hence the above-mentioned safety concerns do not apply.

Accordingly, a problem to be solved by the present invention is to provide an apparatus, a medical device and a method which enable simplified transmission and, if applicable, further recording in order to evaluate operating and machine data of a medical device.

This problem is solved by the subject-matter of the respective independent claims. Advantageous further developments arise from the dependent claims, the present description and the figures.

Accordingly, an apparatus is proposed for transmitting operating and machine data of a medical device, preferably a dialysis device, to an evaluation device, wherein the apparatus comprises a data input for receiving operating and machine data of the medical device, a programmable storage unit which is configured to store at least a portion of the operating and machine data that is received, a voltage input which is configured to supply the apparatus with an operating voltage provided by the medical device, and a transmission unit which is configured to transmit the stored operating and machine data to the evaluation device.

By means of the apparatus, the operating and machine data of the medical device can thus be read out, cached and then passed to the evaluation device. This enables separation in time between the reception and storage of the operating and machine data and its handover to the evaluation device.

By means of the apparatus, there is also electrical isolation between the medical device and the evaluation device, with the result that the medical device is not influenced electrically by the voltage supply and/or the grounding of the evaluation device during the treatment and/or the storage and/or the transmission and/or the evaluation of the operating and machine data by the evaluation device. Accordingly, the reception and storage of the operating and machine data by means of the apparatus can also be carried out during the actual medical treatment of a patient by means of the medical device.

The evaluation device can be a computer, which is preferably portable and is in particular a laptop computer. The evaluation device can also be a mobile terminal, for example a smartphone or a tablet. By means of the apparatus it is possible to capture and forward various operating and machine data from the medical device, without influencing the operation of the medical device and without the need for the evaluation device to remain at the medical device or connected to it during the storage of the operating and machine data. The mobile terminal, for example a smartphone or a tablet, can also be connected between an evaluation device and the apparatus, with the result that the data from the apparatus is transmitted first to the mobile terminal and from there to the evaluation device.

The voltage input of the apparatus is preferably configured to be connected with a voltage output of the medical device, at which the operating voltage is supplied. In other words, the apparatus is supplied with energy via the medical device. In particular, the operating voltage can be used to supply energy to the storage unit and/or the transmission unit. For this purpose the apparatus can have additional electronic components to distribute and/or transform the operating voltage. It is possible that all components of the apparatus are supplied with energy by the operating voltage alone when the apparatus is connected with the medical device. In other words, when the apparatus is connected with the medical device it is not connected with any other voltage source. Alternatively, or additionally, it is possible for the apparatus to have only the voltage input as a supply connection, and be free of any further supply connections that could be connected with another, particularly an external, voltage source.

Energy supply via the medical device, avoiding other voltage sources, can be advantageous particularly in medical applications. In particular, by not using external voltage supplies and being supplied with energy via the medical device, the apparatus has much less influence on the electrical and/or functional safety of the medical device that is to be monitored. In contrast, an alternative device (such as for example a laptop) which is supplied with energy by an external voltage supply requires an energy supply unit that is specially approved for medical applications, and in addition cannot be connected with the medical device during the operation of the medical device, and in particular not during a medical treatment.

According to at least one embodiment, the apparatus comprises a data input for receiving operating and machine data from the medical device. The apparatus preferably comprises a plurality of data inputs. For example, the data input is configured to be connected with a data output of the medical device. The operating and machine data can then be data signals transmitted by means of the data output. If the apparatus has a plurality of data inputs, these can be configured each to be connected with one data output from a plurality of data outputs on the medical device, or with the data outputs of different medical devices. In particular, each data input of the apparatus can be assigned uniquely, preferably biuniquely, to a data output of the medical device.

According to at least one embodiment, the apparatus comprises a programmable storage unit. The storage unit can comprise a processor or microchip for programming and a storage medium. The storage unit comprises for example a microcontroller. In addition, the programmable storage unit can comprise communication connections for the transmission, in particular for the output and/or reception, of the operating and machine data.

The storage unit is configured to store at least a portion of the operating and machine data that it receives. The portion of the operating and machine data that is to be stored can be for example the operating and machine data that needs to be monitored and/or recorded, which is for example of particular importance for the evaluation device. Thus by means of the data input and the programmable storage unit, a data readout process can for example be carried out, in which the operating and machine data of the medical device is received via the data input, and a portion of the operating and machine data that is selected by means of the storage unit is stored in memory. The selection can for example be preconfigured by means of a configuration setting in the storage unit, whereby the configuration setting can be set and/or changed for example by the evaluation device and/or the mobile terminal. It is additionally possible for the operating and machine data that is received to contain an additional configuration parameter, on the basis of which the operating and machine data that is to be stored is determined and the storage is accordingly performed.

Instead of storing selected operating and machine data, it is also possible to store all operating and machine data that is output from the medical device via its data output.

Storage can for example be only temporary, i.e. until the stored operating and machine data is transmitted, in particular in a time-shifted or time-delayed manner, to an evaluation device. In this manner, for example asynchronous transmission of the operating and machine data is enabled, whereby the evaluation device is connected only temporarily with the transmission unit—for example when a service technician with a suitable evaluation device is in the vicinity of the medical device, or when the medical device is not carrying out a treatment.

The data input can be configured to forward the operating and machine data that is received, which has for example been provided at the data output of the medical device, to the evaluation device. To achieve this, the data input can be connected, in an electrically conductive manner and/or with a data link, to the storage unit, preferably to the processor of the storage unit.

According to at least one embodiment, the apparatus comprises a transmission unit. The transmission unit is configured to transmit the stored operating and machine data to the evaluation unit. For example, the transmission unit comprises an antenna for wireless reception of the stored operating and machine data and/or its transmission to the evaluation device. The evaluation device is thereby not connected with the medical device for the transmission of the operating and machine data.

The transmission of the operating and machine data to the evaluation device is carried out at a certain transmission speed. The transmission speed can differ from a reception speed, at which the operating and machine data is received from the medical device via the data input. The reception speed can be the speed at which the operating and machine data is generated, and/or at which it is transmitted from the medical device to the apparatus.

The transmission speed is preferably the maximum speed of the transmission protocol by which the transmission unit is connected with the evaluation device. Because the operating and machine data is consolidated in the storage unit, it can be collected when a connection exists between the transmission unit and the evaluation device, and transmitted at the transmission speed.

The apparatus described here pursues in particular the idea of enabling worldwide support for service technicians in the event that the search for causes proves difficult. For example when operating and machine data is generated in the medical device the service staff and/or an operator of the medical device first sends the known facts of the problem that needs to be analyzed to the service or development engineers of the development department, or informs them of these facts. The development department can then, for example, send to the service staff an apparatus that has been preconfigured by means of a configuration setting. Alternatively, or in addition, it is possible for the development department to send the configuration setting to the service staff in the form of a data file, and the service staff themselves transfer the configuration setting to the apparatus by means of an evaluation device. The apparatus can, in particular by means of the configuration setting, be specifically adapted to the problem that needs to be analyzed and/or it can contain parameters that need to be stored. Configuration can thus always be performed from outside rather than via the medical device itself, with the result that the configuration setting can be applied to the apparatus without any effect on the medical device.

The apparatus preferably has a compact design. The apparatus is for example no greater than palm-sized Due to its compact design, the apparatus can easily be sent, for example by post, and/or can be part of the basic equipment of the service staff. The simple design of the apparatus can enable its use with a wide variety of device types. As well as its use with medical devices for causal analysis, other types of data capture are possible, for example as part of PMCFU studies (PMCFU: Post Market Clinical Follow-Up).

According to at least one embodiment of the apparatus, the transmission unit is configured to receive a configuration setting from an evaluation device, and pass this on to the storage unit. For example, the configuration setting is generated by means of the evaluation device and subsequently transmitted to the transmission unit.

According to at least one embodiment of the apparatus, the portion of the operating and machine data that is to be stored is specified by means of the configuration setting. The configuration setting can in particular contain information about the operating and machine data of the medical device that is to be captured. For example, the storage unit contains operating software that can be adjusted by means of the configuration setting. By means of the operating software, the configuration setting can be compiled and for example converted to control signals. By means of the evaluation device, for example, it is possible to define the operating and machine data of the medical device that will be read out as operating and machine data that is to be captured. This can enable the selective storage of operating and machine data that is received. This operating and/or machine data can be stored in the configuration setting and passed to the apparatus.

According to at least one embodiment, the reception of the configuration setting by the transmission unit is blocked while the medical device is in operation. To achieve this, the apparatus can be configured to receive a transmission of the operating state of the medical device, and in particular to recognize that the medical device is operating. It is then possible to block the reception of data via the transmission unit when the medical device is in operation, for example in the event of a medical treatment. The blocking can for example be carried out by means of a microcontroller which is part of the transmission unit and/or the storage unit. Alternatively or in addition, it is possible for transmission via the transmission unit to be blocked when the medical device is in operation. In particular, all forms of external communication can then be blocked during operation of the medical device.

According to at least one embodiment of the apparatus, the apparatus is configured to be connected with and/or disconnected from the medical device while the medical device is in operation. In particular, the apparatus is configured such that it can be connected to and/or disconnected from the medical device in a mechanically detachable and/or electrically conductive manner while the medical device is in operation. It is further possible that disconnection of the apparatus from the medical device can take place during the data readout process, and/or while the apparatus is being supplied with the operating voltage.

The apparatus is preferably configured to receive transmission of the operating state of the medical device, to recognize that the medical device is operating, and as a result to suspend, in an electrically isolating manner, all conductive connections that are external, i.e. do not lead to the medical device, and/or to disconnect all other voltage sources.

According to at least one embodiment, the apparatus comprises at least one control output, which is configured to send a control signal to a data unit of the medical device. The control signal contains information and/or instructions regarding the operating and machine data that is to be provided by the medical device. The control signal can for example be specified by the configuration setting. In this case the storage unit can be configured to supply the control signal and send it by means of the control output to a control input of the medical device. The control input can then transmit the control signal to the data unit. In this case the control input and the control output can be configured to be connected with each other, in particular in an electrically conductive manner.

The data input and/or the control output can also be, here and hereinafter, physical cables. The exchange of data, i.e. the transmission of the operating and machine data and/or the transmission of the control signal, can also take place by means of at least one, and in particular two cables, and/or by means of a CAN bus. The communication along a cable can be bi-directional.

By means of the control signal, the apparatus can for example request special operating and machine data, which can be useful for causal analysis. Alternatively or in addition, it is possible by means of the control signal to specify measures to prevent a communication overload when data is requested. This is in particular facilitated by the ability to identify unambiguously the operating mode of the medical device.

According to at least one embodiment of the apparatus, the storage unit has a processing unit for processing at least a portion of the operating and machine data. This processing preferably takes place prior to the storage of the portion of the operating and machine data that is to be stored. The portion of the operating and machine data that is processed is preferably the portion of the operating and machine data that is to be stored and/or has been stored. The processing unit can for example be configured to process the operating and machine data further. The processing of the stored operating and machine data can comprise the compression of the operating and machine data. This can enable time to be saved during data transmission.

It is additionally possible for at least a portion of the stored operating and machine data to be averaged and/or encrypted during processing. The processing of the operating and machine data can also comprise an evaluation of the operating and machine data. For example the operating and machine data is compressed in the course of an evaluation, and/or reduced in that only operating and machine data that lies outside a predetermined normal range is stored. Alternatively or in addition, the processing unit can add a time stamp and/or a date to at least a portion of the operating and machine data. By this means it can be possible to document the time at which the operating and machine data was generated.

According to at least one embodiment of the apparatus, the transmission unit is a wireless transmission unit. The wireless transmission unit is preferably based on a low energy emission standard, for example Bluetooth. This can enable electromagnetic compatibility and/or a reduction in electromagnetic pollution. The transmission unit comprises for example a Bluetooth transmitter. The term "transmitter" is to be understood here and hereinafter as not excluding the possibility of receiving operating and machine data. In this case it is possible for the wireless transmission unit to be configured such that it can be blocked or switched off during a treatment mode, i.e. in particular during treatment of patients. For this purpose, for example a signal is sent from the medical device to the apparatus during the treatment. Alternatively or in addition, it is possible for the medical device to transmit a date and/or a time stamp, by means of which the current operating state of the medical device is described. The apparatus can recognize from this whether a treatment is currently taking place. The apparatus can be configured to check whether such a signal has been received from the medical device. The apparatus can further be configured to respond to the receipt of an appropriate signal by either limiting external communication to transmission, or preventing all such communication. This can be achieved by the apparatus partially or fully deactivating the transmission unit.

According to at least one embodiment of the apparatus, the transmission unit, which is in particular a wireless transmission unit, is configured to receive configuration data from the evaluation device while the apparatus is connected with the medical device. Alternatively or in addition, the transmission unit, which is in particular a wireless transmission unit, is configured to transmit the stored operating and machine data to the evaluation device while the apparatus is connected with the medical device. For this purpose, the transmission unit and/or the evaluation unit can for example have a wireless transmitter, such as for example a Bluetooth transmitter. This can make it possible to transmit the configuration setting to the apparatus, or read out the stored operating and machine data from the apparatus, without the need to disconnect the apparatus from the medical device. The transmission unit can be configured to enable the receipt of configuration data and/or the output of the stored operating and machine data during the operation of the medical device. By this means, secure and undisrupted operation of the medical device together with efficient causal analysis can be ensured.

According to at least one embodiment of the apparatus, it is designed as a type of dongle. Here and hereinafter, a dongle can be a compact hardware component. A dongle can have a compact design. A dongle can be configured for example to connect with a system, wherein the system can be provided with additional functions by means of the dongle. The apparatus can then be for example designed to be at most palm-sized. For example, the apparatus extends a maximum of 10 cm in each spatial direction, preferably a maximum of 8 cm, and particularly preferably a maximum of 5 cm. Due to its compact design, the apparatus requires little space. Furthermore, particularly due to the compact design of the apparatus, the risks of its contamination, for example by germs and/or chemical substances, are reduced.

According to at least one embodiment, the apparatus comprises a first connecting component. This first connecting component can comprise a communication interface and an energy supply interface. The communication interface comprises the data input and/or the control output, if any. The energy supply interface comprises the voltage input. The data input, the voltage input and/or the control output can be connections of the first connecting component.

The first connecting component can be suitable to be plugged into a second connecting component of the medical device. The second connecting component of the medical device can be a service interface of the medical device. The first connecting component can be designed as a type of female connector, and the second connecting component can be designed as a type of male connector, in particular one which cooperates with the first connecting component, or vice versa. For example the first connecting component is a plug and the second connecting component is a receptacle, or vice versa.

The first connecting component and the second connecting component are for example a D-Sub connector pair or a USB connector pair, wherein a connector pair here and hereinafter can be the combination of a male and a female connector of a mechanical plug-in connection. The first connecting component can then be for example a D-Sub plug or a USB plug. In particular, the first connecting component can be suitable for a CAN bus connection.

According to at least one embodiment, the first connecting component is configured to connect the apparatus with the medical device in a mechanically detachable and/or electrically conductive manner. A "mechanically detachable connection" is to be understood here and hereinafter as a mechanical connection between two components which can be detached non-destructively, i.e. without destroying the components, and preferably without additional tools, such as screwdrivers, or solvent. The electrically conductive connection can be established via the voltage input. In addition, an electrically conductive connection is possible via the data input, for example for transmission of electrical data signals.

According to at least one embodiment, the first connecting component is designed such that a ground connection of the apparatus is connected with a ground connection of the medical device. In particular, the apparatus and the medical device can be on the same electrical potential and shielded from the outside.

The first connecting component can have a connector housing, in which the connections of the first connecting component are disposed. The connector housing can be designed to be electrically insulating and/or electrically shielding. By means of the connector housing the connections can be provided with contact protection. The connector housing can have a one-piece or multi-piece design, with the one-piece design preferred due to its greater ease of operation. A "multi-piece connector housing" is understood here and hereinafter to exist if the connector housing is formed with, or consists of, a plurality of spatially separated components. In this case, one or some of the connections of the first connecting component, for example the data input, can be disposed in a first connector housing, while the remaining connections are disposed in a second connector housing and/or possible further housings of the first connecting component. In a "one-piece connector housing", all connections of the first connecting component are disposed in a single connector housing. A one-piece connector housing can be formed in a single piece or from a plurality of parts directly adjacent to each other.

According to at least one embodiment of the apparatus, it comprises a housing designed to be electrically insulating, which contains at least the storage unit and the transmission unit. The housing can contain or consist of an encapsulation or enclosure of the electronic components of the apparatus.

Alternatively or in addition, the housing can have or consist of a plastic container. It is possible for the housing to be disposed directly adjacent to, or be formed in a single piece with, the connector housing, if such is present, of the first connecting component, if such is present. By means of the housing, the electrical components of the apparatus can be protected for example from external influences that could potentially pose a risk to the operation of the apparatus and/or the medical device. The housing can serve as contact protection for the apparatus. By this means it is possible to prevent a spark discharge caused by touch, or electrical contamination of the apparatus and/or the medical device.

A medical device, preferably for carrying out a dialysis treatment, is further proposed. The medical device is for example a dialysis device for monitoring and/or performing a dialysis treatment. The medical device is preferably configured to be connected with an apparatus such as described here for transmitting operating and machine data to an evaluation device. This means that all features of the apparatus that are described here are disclosed for the medical device, and vice versa.

According to at least one embodiment of the medical device, it comprises a data output for sending operating and machine data of the medical device to an apparatus, preferably the apparatus previously described. In particular, the data output can be configured to be connected, preferably in a mechanically detachable and/or electrically conductive manner, with the data input of the previously described apparatus.

According to at least one embodiment, the medical device comprises a voltage output, which is configured to output an operating voltage to supply the apparatus. It is possible that the operating voltage is output during the entire time that the medical device is in operation. Alternatively, it is possible that the medical device has a voltage unit for monitoring the voltage output. By means of this it is possible to output the operating voltage only when the apparatus is plugged into the medical device and/or a switching signal is applied at the other connection. For example, the switching signal can be applied by the apparatus at the other connection. Due to the fact that constant application of a voltage at the voltage output is avoided by the use of a voltage unit, the safety of the medical device during operation can for example be increased.

According to at least one embodiment, the medical device comprises a data unit, which is configured to supply the operating and machine data at the data output depending on a control signal. "Depending on a control signal" means here and hereinafter that the content of the multiplicity of operating and machine data that the data unit supplies at the data output is varied depending on the control signal. The content of the multiplicity of operating and machine data can be for example a type of data, signals and/or parameters contained in the operating and machine data, a range of operating and machine data, and/or a duration of the data output. The control signal can be specified by a configuration setting, which can be a configuration setting previously described in connection with the apparatus, and which is stored in the apparatus, particularly in the storage unit. The medical device further comprises for example a control input which can be connected with a control output of the apparatus. The control signal can then be supplied via the control output, and passed via the control input of the medical device to the data unit.

According to at least one embodiment of the medical device, it comprises a second connecting component. This second connecting component has a voltage output. The second connecting component can further comprise the data output. The second connecting component preferably comprises a plurality of data outputs, for instance as part of a CAN bus system. The second connecting component is configured to accommodate a first connecting component of an apparatus for transmitting operating and machine data of the medical device, or to be connected with the first connecting component. In particular, by means of the second connecting component and the first connecting component, the medical device can be connected with the apparatus in a mechanically detachable and/or electrically conductive manner. The second connecting component is for example a CAN bus connector, which can contain at least one CAN bus, in particular two CAN buses.

A method is further proposed for transmitting operating and machine data of a medical device, preferably a dialysis device, to an evaluation device. The method is preferably used for transmitting operating and machine data of a medical device described here. Further, the method is preferably carried out with an apparatus described here. This means that all features that are disclosed for the apparatus and/or the medical device are disclosed for the method, and vice versa.

According to at least one embodiment of the method, an apparatus is provided. The apparatus comprises a data input, a programmable storage unit, a voltage input and a transmission unit. The apparatus is preferably the apparatus previously described.

According to at least one embodiment of the method, the apparatus is connected, preferably in a mechanically detachable and/or electrically conductive manner, with the medical device. The connection is such that the apparatus is supplied via the voltage input with an operating voltage provided by the medical device. The connection can further be made by means of the first connecting component of the apparatus, if such is present, for example by plugging the first connecting component into a second connecting component of the medical device. The connection of the apparatus with the medical device can also be made such that the data input is connected with a data output of the medical device. Alternatively or in addition, the connection can be made such that a voltage input of the apparatus is connected with a voltage output of the medical device.

According to at least one embodiment of the method, it comprises reception via the data input of operating and machine data of the medical device. The operating and machine data can for example be provided at the data output of the medical device. A portion of the operating and machine data is stored by means of the storage unit. The operating and machine data can for example be processed by a processing unit of the apparatus before it is stored.

According to at least one embodiment of the method, the stored operating and machine data is transmitted to an evaluation device. The transmission takes place by means of the transmission unit. The transmission can be carried out while the apparatus is connected with the medical device. Alternatively, it is possible that the apparatus is disconnected from the medical device prior to transmission, and subsequently connected with the evaluation device, preferably in a mechanically detachable and/or electrically conductive manner.

According to at least one embodiment of the method, the apparatus is supplied via the voltage input with an operating voltage provided by the medical device via the voltage output. When the apparatus is connected with the medical device, it is preferably supplied exclusively by means of the operating voltage that is applied at the voltage output.

According to at least one embodiment, the method further comprises the steps of connecting the apparatus with an evaluation device and transmitting a configuration setting from the evaluation device to the storage unit. These steps are preferably carried out by means of the transmission unit. For this purpose, for example an electrically conductive or wireless connection is established between the transmission unit and the evaluation unit. In the case of a wireless connection, the transmission unit can be a wireless transmission unit and the evaluation device can have a wireless transmitter. By means of the transmission unit, the configuration setting can then be transmitted to the apparatus and the configuration setting can be passed on to the storage unit. The apparatus is preferably disconnected from the evaluation device after transmission of the configuration setting.

According to at least one embodiment of the method, the transmission of the configuration setting, and in particular the connection of the apparatus to the evaluation device, is carried out while the apparatus is connected with the medical device. Alternatively or in addition, the transmission of the stored operating and machine data to the evaluation device is carried out while the apparatus is connected with the medical device. In other words, the transmission of the configuration setting, and/or the possible transmission of the stored operating and machine data, takes place after the connection of the apparatus with the medical device and prior to disconnection of the apparatus from the medical device. The transmission of the configuration setting and/or the stored operating and machine data can in particular take place while the medical device is in operation.

It is in particular possible for the transmission unit to be a wireless transmission unit. In this case the stored operating and machine data can be transmitted to the evaluation device by means of the wireless transmission unit while the apparatus is connected with the medical device. Furthermore, the configuration setting can be transmitted to the apparatus by means of the wireless transmission unit while the apparatus is connected with the medical device. For this purpose the evaluation unit can have a wireless transmitter which transmits the configuration data to the transmission unit.

According to at least one embodiment of the method, the connection of the apparatus to the medical device takes place while the medical device is in operation. Alternatively or in addition, disconnection of the apparatus from the medical device takes place, in a possible further step, while the medical device is in operation. The connection and/or disconnection of the apparatus to or from the medical device thus preferably has no influence on the operation, and in particular the safe operation, of the medical device. The apparatus can thus for example be plugged into or unplugged from the medical device during the performance of a medical treatment, in particular a dialysis treatment. By this means, causes can be analyzed and problems rectified without the treatment being ended, which is a lengthy and not always feasible process. In particular, operating and machine data that is generated during the treatment can be instantly examined.

According to at least one embodiment of the method, it further comprises provision of the evaluation device, which has an input interface. The input interface can be for example a keyboard and/or a touchscreen in combination with application software in the evaluation device, in particular software with a graphic display, such as for example an app. The method further comprises input of the configuration data in the evaluation device by means of the input interface. For example all possible configuration settings are displayed on a screen of the evaluation device in a form of graphical checklist, and can be selected by a user, such as for example a service technician or the development department.

According to at least one embodiment of the method, it further comprises additional processing of the stored operating and machine data by means of the evaluation device. The evaluation device can for example be identical to the evaluation device described here. For example, by means of the evaluation device the stored operating and machine data is displayed graphically, stored, compressed, organized and/or otherwise processed. The evaluation device can further have internet access and/or fax access. This makes it possible for example to send the stored operating and machine data by email and/or fax, and/or to access an information database of the manufacturer of the medical device by means of the evaluation device. The evaluation device can for example have application software for processing the stored operating and machine data. It is in particular possible that the transmission of the stored operating and machine data takes place simultaneously with the storage of (in particular additional) operating and machine data. By this means, for example during the readout of the operating and machine data, a check can be performed to determine whether the configuration setting is appropriate for causal analysis, and the configuration setting can be adjusted if necessary.

BRIEF DESCRIPTION OF THE FIGURES

The apparatus described here, the medical device described here, and the method described here are explained in more detail below with the aid of example embodiments and the associated figures.

DETAILED DESCRIPTION OF THE FIGURES

In the figures, elements which are identical or similar, or have identical effects, are designated with identical reference signs. The figures, and the relative proportions of the elements shown in the figures, are not true to scale. The size of individual elements may instead be exaggerated in order to show them more clearly and/or improve understandability.

Figure 1:
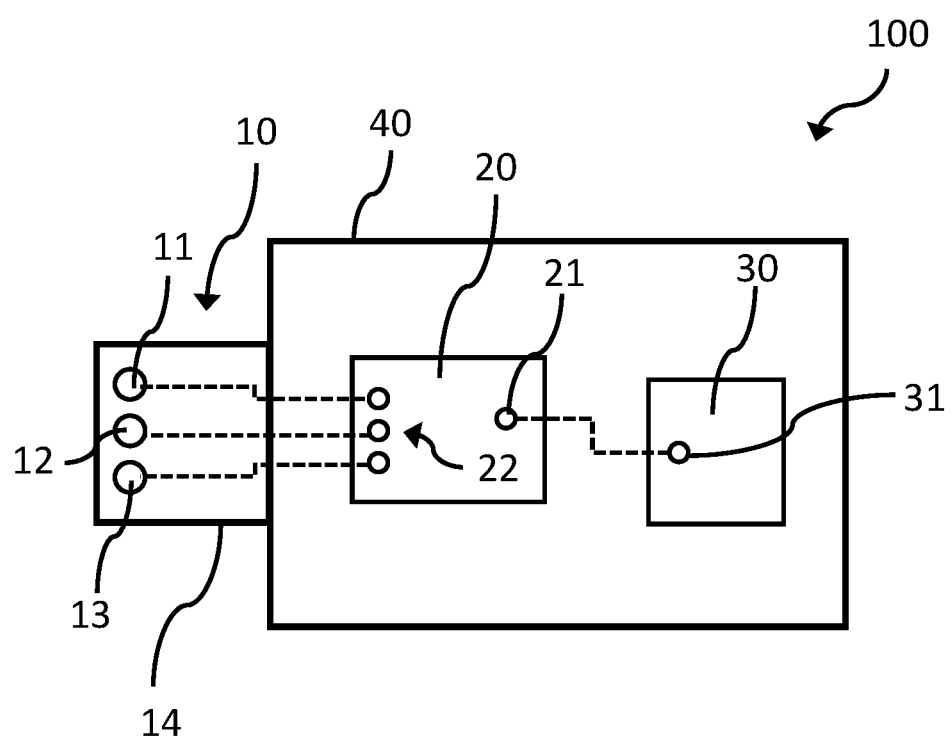
FIGS. 1 and 2 show schematically examples of embodiments of an apparatus described here, using schematic representations.

An example embodiment of an apparatus 100 described here is explained in more detail with the aid of the schematic representation in FIG. 1. Apparatus 100 is represented in the example embodiment of FIG. 1 as a type of dongle, which can be connected with a suitable data output for transmitting operating and machine data of a medical device.

The apparatus 100 serves to store operating and machine data of a medical device 500, which can be for example a dialysis device. The apparatus can further be configured to transmit operating and machine data to an evaluation device. The apparatus comprises a data input 12 for receiving operating and machine data of the medical device 500, a programmable storage unit 20 which is configured to store at least a portion of the operating and machine data that is received, and a transmission unit 30 which is configured to transmit the stored operating and machine data to the evaluation device. A voltage input 11 is further provided, which is configured to supply the apparatus 100 with an operating voltage provided by the medical device 500.

The programmable storage unit 20 comprises in particular a storage device, for example a non-volatile memory and a processor or microchip. The processor or microchip is configured to support the storage process and/or to process data and/or to carry out the communication. The processor or microchip can be programmed using configuration settings, and thereby, among other functions, also serves as a processing unit for processing operating and machine data.

The apparatus 100 also comprises a first connecting component 10 with the voltage input 11 and signal lines 12, 13. Signal lines 12, 13 can be a data input 12 and a control output 13. It is however also possible for the signal lines 12, 13 to be a bidirectional interface, in particular a single bidirectional interface, such as for example in the case of a CAN bus. Only one connection is shown here in each case, purely by way of example. In the example embodiment that is shown, the first connecting component 10 is a plug connector, which is designed in accordance with the design of the corresponding socket of the medical device.

The first connecting component 10 can in particular also have a plurality of data inputs 12 and/or control outputs 13, which correspond with the respective data outputs and control inputs on the applicable medical device. For example the connecting component 10 can have separate signal lines 12, 13 for operational control communication and for protection system communication with the medical device. By means of such a design the apparatus 100 can be adapted to the internal communication structure of the medical device. The medical device has for example two separate CAN buses: one for the operational control communication of the medical device and another for the protection system communication of the medical device The first connecting component 10 can also be designed with data inputs 12 and/or control outputs 13 for different medical devices, so that the apparatus 100 can be configured to transmit operating and machine data from differing types of medical device.

In addition, the voltage input 11 is shown schematically as a single connection, which however contains at least two poles and possibly a grounding element, in order to provide the voltage supply to the apparatus 100 when it is connected with the medical device. The voltage input 11 can also be designed to be compatible with a plurality of medical devices.

The first connecting component 10 also comprises a connector housing 14, which encloses the other components of the first connecting component 10 and connects them with each other. In the example embodiment shown in FIG. 1, the connector housing 14 is formed in a single piece. All connections of the first connecting component 10 are thus disposed in a single connector housing 14. The connector housing 14 and the connections disposed within it form together a plug connector, which corresponds to the socket provided by the medical device.

The apparatus 100 further comprises a housing 40, on which the connector housing 14 is disposed, and in which the storage unit 20 and the transmission unit 30 are disposed.

The storage unit 20 is connected with the voltage input 11, the data input 12 and the control output 13 of the first connecting component 10. Between the voltage input 11 and the transmission unit 30 there is a possible electrical connection, not shown in FIG. 1, via which the transmission unit 30 can also be supplied with electrical energy. Thus the storage unit 20 can store operating and machine data that is provided via the data input 12. The operating and machine data can thereby be received from the medical device at the data input 12 over a predetermined period and stored in the storage unit 20. The operating and machine data is accordingly accumulated in the storage unit 20.

In a preferred embodiment, the operating and machine data that is received from the medical device is in each case given a time stamp when it is stored in the storage unit 20.

The storage unit 20 is connected via a first transmission connection 21 with a second transmission connection 31 of the transmission unit 30. Accordingly the transmission unit 30 can communicate with the storage unit 20, and receive the operating and machine data that is stored in the storage unit 20, which it can then transmit to an evaluation device (not shown here).

When the operating and machine data is stored in the storage unit 20 over a certain period, a time-delayed transmission of the operating and machine data to the evaluation device can be carried out by means of the transmission unit 30. In this case the operating and machine data that has been stored in the storage unit 20 over a predetermined period is in particular transmitted all at once to the evaluation device, for example whenever a service technician is present and the transmission unit 30 is in communication with an evaluation device that is used by the service technician. The transmission can take place at specific times, for example when the medical device signals that a treatment has been finished.

The transmission unit 30 can be designed as a wireless transmission unit 30, by means of which the operating and machine data that is stored in the storage unit 20 can be transmitted wirelessly to the evaluation unit. Suitable transmission protocols are those that have low electromagnetic emissions, for example short-range transmission protocols such as Bluetooth.

The transmission unit 30 can however also be designed in the form of a plug-in connection, wherein the plug-in connection formed by the first connecting component 10 can also be used for transmitting the operating and machine data by means of the transmission unit 30.

The apparatus 100 can have additional components, in particular additional connections.

Figure 2:
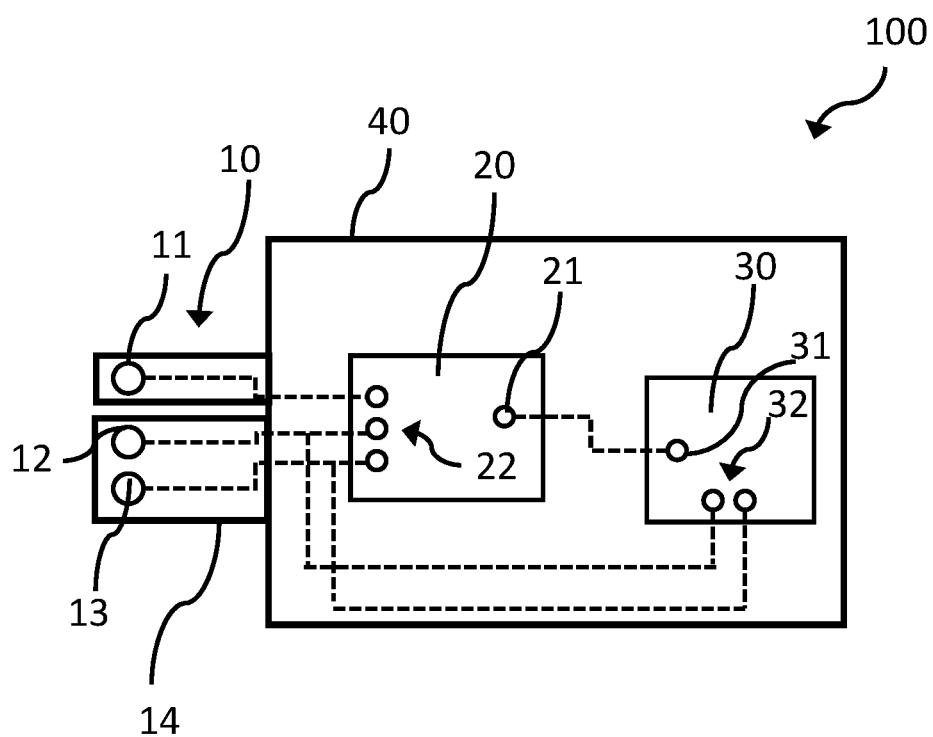

A further example embodiment of an apparatus 100 described here is explained in more detail with the aid of the schematic representation in FIG. 2. The example embodiment in FIG. 2 differs from that in FIG. 1 in the mechanical design of the first connecting component 10, as follows.

The first difference is that the connector housing 14 of the apparatus 100 in the example embodiment in FIG. 2 has a multi-piece design. In particular, the voltage input 11 is disposed in a first part of the connector housing and both the data input 12 and the signal output 13 are disposed in a second part of the connector housing. The two parts of the connector housing are designed to be spatially separated from each other and/or electrically insulated from each other. Alternatively or in addition to what is shown in FIG. 2, it is possible that one part of the connector housing is disposed on a side of the housing 40 of the apparatus that is facing away from another part of the connector housing.

In the example embodiment shown in FIG. 2, the transmission unit 30 has additional connectors 32, and the storage unit 20 has connectors 22, that are connected with the data input 12 and the control output 13. This enables, for example, a wired connection of the apparatus 100 with the evaluation device by means of the first connecting component 10. Alternatively, the apparatus 100 can have a further connecting component, for instance an additional plug, which can serve to connect the apparatus 100 with the evaluation device.

Figure 3:
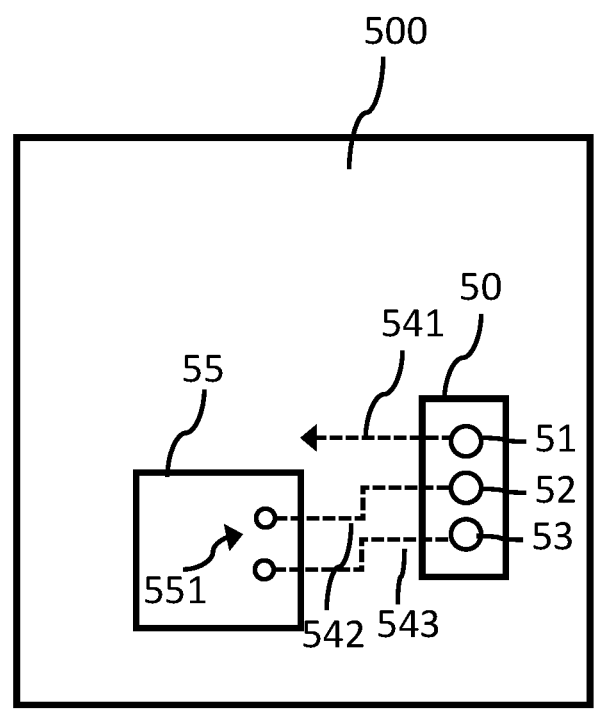
FIGS. 3 and 4 show schematically examples of embodiments of an apparatus described here and a medical device described here, using schematic representations.

An example embodiment of a medical device 500 is explained in more detail with the aid of the schematic representation in FIG. 3. The medical device 500 is preferably a dialysis device for carrying out a dialysis treatment, for example for carrying out hemodialysis, hemofiltration, hemodiafiltration, peritoneal dialysis, acute dialysis, liver assist therapy, apheresis and/or another dialysis treatment.

The medical device 500 comprises a second connecting component 50 with a voltage output 51, a data output 52 and a control input 53. The second connecting component 50 can comprise further data outputs and control inputs (which are not shown in the Figures). The medical device 500 further comprises a first connection 541, a second connection 542, a third connection 543, a data unit 55 and data connectors 551.

The second connecting component 50 is designed to receive a first connecting component 10 of an apparatus 100, in particular the apparatus 100 of the example embodiment in FIG. 1. In particular, the voltage output 51, the data output 52 and/or the control input 53 are designed to connect with a voltage input 11, a data input 12 and/or a control output 13 respectively of the apparatus 100.

By means of the medical device 500, an operating voltage which is suitable for supplying energy to the apparatus 100 can be applied via the first connection 541 to the voltage output 51. Via the second connection 542 and the third connection 543, the data output 52 and/or the control input 53 respectively are connected with the data unit 55.

Figure 4:
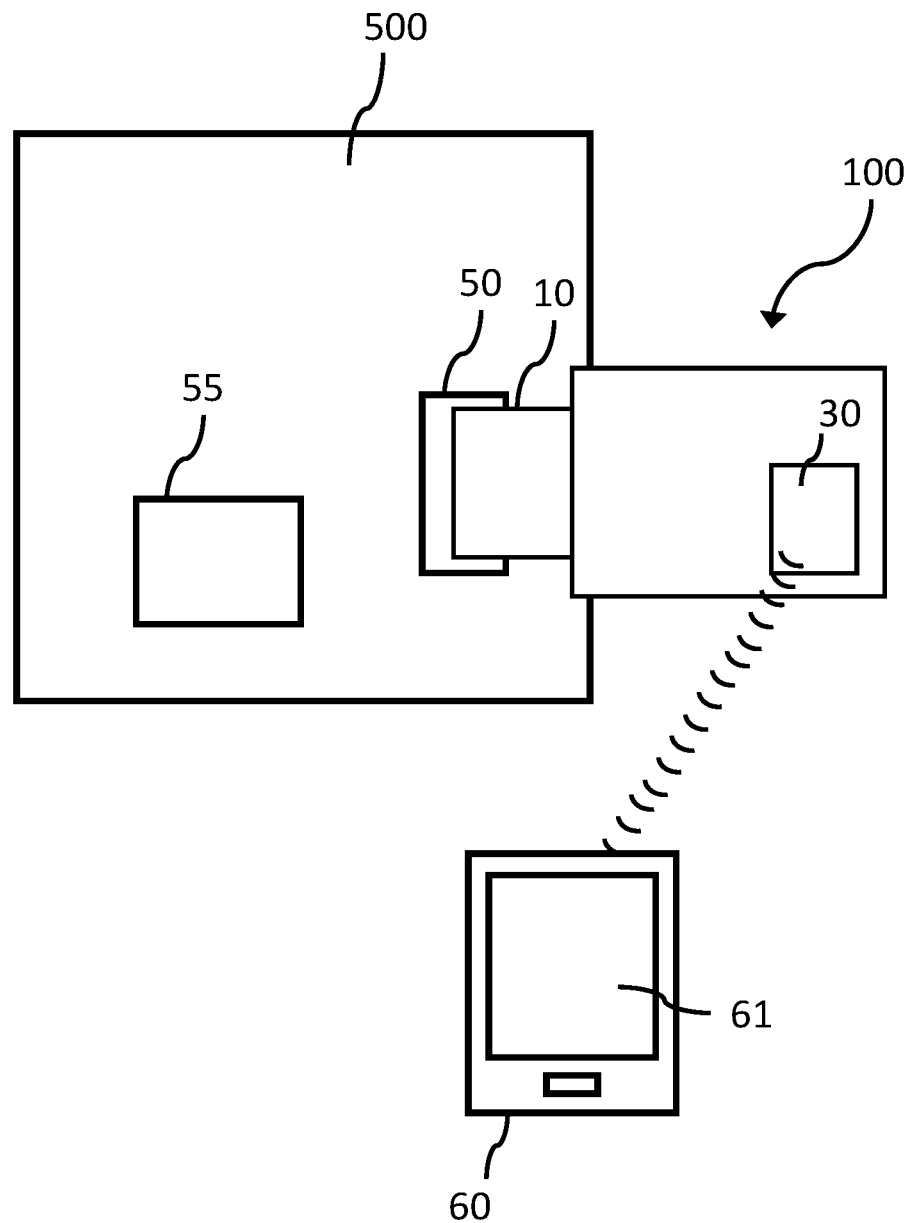

An example embodiment of an apparatus 100 described here and a medical device 500 described here is explained in more detail with the aid of the schematic representation in FIG. 4. The figure shows an apparatus 100 according to the example embodiment of FIG. 1, which is plugged by means of the first connecting component 10 into the second connecting component 50 of a medical device 500 according to the example embodiment of FIG. 3. For clarity, FIG. 4 does not show the connections of the apparatus 100, in particular of the first connecting component 10, or the connections of the medical device 500, in particular of the second connecting component 50.

Also shown is an evaluation device 60, which comprises a wireless transmitter unit and an input interface 61. The evaluation device 60 can for example be provided in the form of a mobile terminal such as a smartphone or a tablet. The evaluation device 60 is thereby not in electrical contact with the medical device 500. Instead it receives the operating and machine data that is stored in the storage unit 20 wirelessly via the transmission unit 30.

In the event that no wireless interface is available and, in another example embodiment, the transmission takes place via the plug of the first connecting component 10 by means of plugging the apparatus 100 into the evaluation device 60, the evaluation device 60 will again not be in electrical contact with the medical device 500, since the apparatus 100 can only be plugged into either the medical device 500 or the evaluation device 60.

Accordingly, time-delayed or asynchronous transmission of operating and machine data takes place from the medical device 500 to the evaluation device 60, without the existence of any electrical contact between the evaluation device 60 and the medical device 500.

Figure 5:
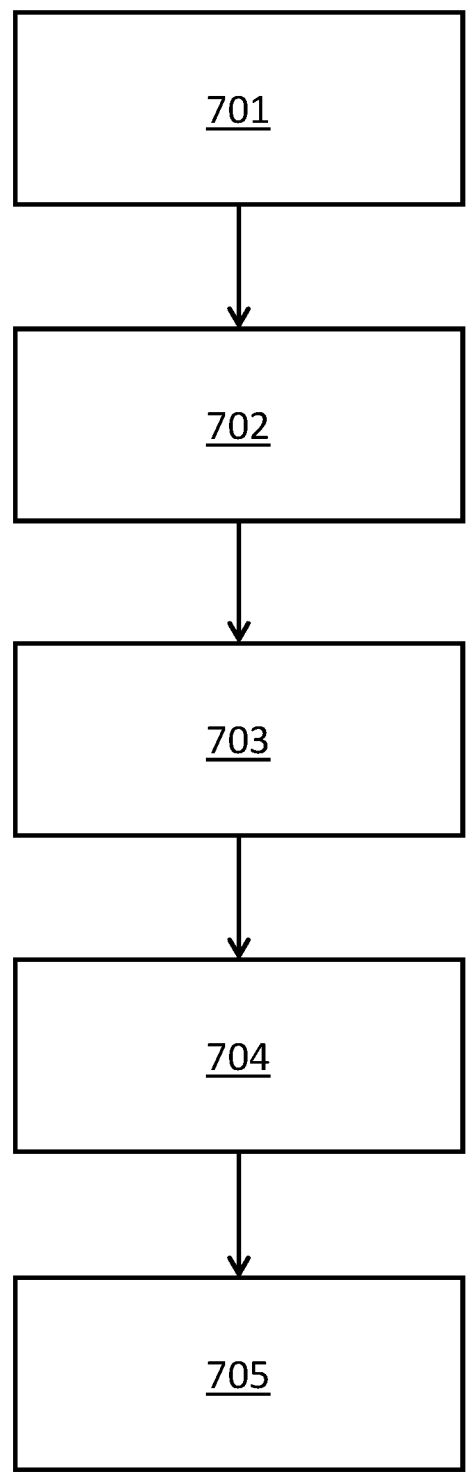
FIG. 5 shows an example embodiment of a method described here, using a schematic representation.

An example embodiment of a method described here is explained in more detail with the aid of the schematic representation in FIG. 5. The transmission of the operating and machine data of the medical device 500 to the evaluation device 60 can for example take place as follows. In a first method step 701, by means of the evaluation device 60 a configuration setting is sent to the wireless transmission unit 30 of the apparatus 100. From here it is passed to the storage unit 20. In a second method step 702, the configuration setting is compiled in the storage unit 20 and a control signal is generated. This is sent via the control output 13 of the apparatus 100 to the control input 53 of the medical device 500, and passed on via the first connection 541 to the data unit 55. In accordance with the control signal, the data unit 55 provides operating and machine data, which it outputs via the second connection 542 to the data output 52. Here the operating and machine data is passed on to the storage unit 20 via the data input 12 of the device 100 (third method step 703). If necessary the storage unit 20 extracts only a portion of the operating and machine data from the operating and machine data that it has received, and stores the extracted portion. The extraction or filtering-out of the operating and machine data that is to be stored from the entirety of the operating and machine data that is received takes place according to the configuration setting. It is however also possible that the storage unit 20 saves all of the operating and machine data as stored operating and machine data.

Alternatively, it is possible that no control signal is sent to the data unit 55, or that no data unit 55 is provided. In this case, the medical device 500 always provides the same operating and machine data, independently of the configuration setting. The storage unit 20 then extracts the portion of the operating and machine data that is to be stored, according to the configuration setting.

In an additional fourth method step 704, which is preferably performed prior to storage, the stored operating and machine data can if necessary be processed or otherwise prepared, for example by encryption or averaging of the operating and machine data. In a fifth method step 705, the operating and machine data, which has thereby been processed and—preferably subsequently—stored, is transmitted by means of the transmission unit 30 to the evaluation device. The transmission of the stored operating and machine data can take place during the data readout process. Alternatively, transmission can be delayed, i.e. it can take place after storage is completed.

In a further preferred embodiment, all operating and machine data that is generated in the medical device 500 during the operation of the medical device 500 is read out by the apparatus 100 at the data output 52 of the medical device 500, and received at the data input 12 of the apparatus 100. Transmission of control data from the apparatus 100 to the medical device 500 is therefore unnecessary. Accordingly, the apparatus 100 merely "eavesdrops" on the operating and machine data that is generated in the medical device 500, for example by monitoring a suitable bus. In this case it is possible to dispense with the implementation of the control output 13 of the first connecting component 10 of the device 100, and thereby also the implementation of the control input 53 in the medical device 500.

The description of the invention with the aid of example embodiments does not limit the invention to these embodiments. Instead, the invention comprises every new feature as well as every combination of features, which, in particular, includes every combination of features in the patent claims, even if such feature or combination is not specified explicitly in the patent claims or the example embodiments.

LIST OF REFERENCE SIGNS 100 apparatus
10 first connecting component
11 voltage input
12 data input
13 control output
14 connector housing
20 storage unit
21 first transmission connection
22 connections
30 transmission unit
31 second transmission connection
32 connections of the transmission unit
40 housing 500 medical device
50 second connecting component
51 voltage output
52 data output
53 control input
541 first connection
542 second connection
543 third connection
55 data unit
551 data connectors
60 evaluation device
61 input interface
701 first method step
702 second method step
703 third method step
704 fourth method step
705 fifth method step

The invention claimed is:

1. An apparatus for transmitting operating and machine data of a medical device to an evaluation device, wherein the apparatus comprises:
   a data input for receiving operating and machine data of the medical device,
   a programmable storage unit that is configured to store at least a portion of the operating and machine data that is received from the medical device,
   a voltage input that is configured to supply the apparatus with an operating voltage provided exclusively by the medical device, and
   a transmission unit that is configured to transmit the stored operating and machine data to the evaluation device, wherein
   the operating voltage provided exclusively by the medical device is used to supply energy to the programmable storage unit and the transmission unit,
   the transmission unit is configured to receive a configuration setting from the evaluation device, and to pass the configuration setting on to the programmable storage unit,
   the configuration setting comprises information about the operating and machine data of the medical device, which is to be captured,
   the programmable storage unit is configured by the configuration setting to selectively store the operating and machine data according to the configuration setting,
   the reception of the configuration setting by the transmission unit is blocked while the medical device is in operation, and
   the apparatus is configured to be mechanically connected with and mechanically detachable from the medical device.

2. The apparatus according to claim 1, wherein the apparatus is configured to be mechanically connected with and/or mechanically detachable from the medical device while the medical device is in operation.

3. The apparatus according to claim 1, wherein the storage unit has a processing unit for processing at least a portion of the operating and machine data.

4. The apparatus according to claim 1, wherein the transmission unit is configured to transmit the operating and machine data that is stored in the storage unit wirelessly to the evaluation unit.

5. The apparatus according to claim 1, wherein the apparatus is designed as a type of dongle.

6. The apparatus according to claim 1, comprising a housing designed to be electrically insulating, which contains the storage unit and the transmission unit.

7. In combination, the apparatus according to claim 1 and a medical device, the medical device comprising a data output and a voltage output, wherein: the data output is configured for sending operating and machine data of the medical device to the apparatus; and the voltage output, is configured to exclusively provide an operating voltage to supply energy to the apparatus.

8. A method for transmitting operating and machine data of a medical device to an evaluation device, said method having the following steps:
   providing an apparatus comprising a data input, a programmable storage unit, a voltage input, and a transmission unit;
   mechanically connecting the apparatus with the medical device such that the apparatus is supplied via the voltage input with an operating voltage provided exclusively by the medical device, wherein the operating voltage provided exclusively by the medical device is used to supply energy to the programmable storage unit and the transmission unit of the apparatus;
   receiving, by the transmission unit, a configuration setting from the evaluation device, the configuration setting comprising information about the operating and machine data of the medical device, which is to be captured;
   receiving the operating and machine data of the medical device via the data input;
   passing the configuration setting on to the programmable storage unit;
   storing at least a portion of the operating and machine data according to the configuration setting, in the programmable storage unit; and
   transmitting the stored operating and machine data to the evaluation device by means of the transmission unit, wherein
   the reception of the configuration setting by the transmission unit is blocked while the medical device is in operation, and
   the apparatus is configured to be mechanically connected with and mechanically detachable from the medical device.

9. The method according to claim 8, wherein the receiving the configuration setting and passing the configuration setting to the programmable storage unit further comprises connecting the apparatus with the evaluation device.

10. The method according to claim 9, wherein the transmission of the configuration setting from the evaluation device and/or the transmission of the stored operating and machine data to the evaluation device is carried out while the apparatus is connected with the medical device.

11. The method according to claim 8, wherein the mechanical connection of the apparatus with the medical device and/or mechanical detachment of the apparatus from the medical device is carried out while the medical device is in operation.

12. The apparatus of claim 1, wherein said apparatus is a dialysis device.

13. The apparatus according to claim 1, wherein the transmission unit is configured to transmit the operating and machine data that is stored in the storage unit wirelessly to the evaluation unit, while the apparatus is connected with the medical device.

14. The medical device of claim 7, wherein said medical device is for dialysis treatment.

15. The method of claim 8, wherein said medical device is a dialysis device.

\* \* \* \* \*